(12) United States Patent
Kannan et al.

(10) Patent No.: US 11,614,433 B2
(45) Date of Patent: *Mar. 28, 2023

(54) SYSTEMS AND METHODS TO TRACK CLEANLINESS OF VEHICLE EXTERIOR AND REDUCE OPERATING EXPENSES

(71) Applicant: GM Cruise Holdings LLC, San Francisco, CA (US)

(72) Inventors: Sriram Salem Kannan, Pacifica, CA (US); Maximilian Gerrit Euchenhofer, Phoenix, AZ (US)

(73) Assignee: GM CRUISE HOLDINGS LLC, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/512,938

(22) Filed: Oct. 28, 2021

(65) Prior Publication Data

US 2022/0057374 A1 Feb. 24, 2022

Related U.S. Application Data

(63) Continuation of application No. 16/687,029, filed on Nov. 18, 2019, now Pat. No. 11,187,688.

(51) Int. Cl.
*G01N 33/00* (2006.01)
*G06Q 10/20* (2023.01)
*G06V 20/59* (2022.01)

(52) U.S. Cl.
CPC ......... *G01N 33/0075* (2013.01); *G06Q 10/20* (2013.01); *G06V 20/59* (2022.01)

(58) Field of Classification Search
None
See application file for complete search history.

(56) References Cited

U.S. PATENT DOCUMENTS 11,187,688 B2 * 11/2021 Kannan ............ G01N 33/0075

* cited by examiner

*Primary Examiner* — Roy Y Yi
(74) *Attorney, Agent, or Firm* — Akona IP (57) ABSTRACT

Systems and methods are provided for dynamically tracking the cleanliness of a vehicle's exterior. In particular, a dynamic strategy for cleaning vehicles is provided. In a system including a fleet of vehicles, the vehicles are regularly cleaned to remove dirt, dust, and any other matter that has stuck to the vehicle.

20 Claims, 8 Drawing Sheets

SYSTEMS AND METHODS TO TRACK CLEANLINESS OF VEHICLE EXTERIOR AND REDUCE OPERATING EXPENSES

CROSS-REFERENCE TO RELATED APPLICATION

This application is a continuation of U.S. patent application Ser. No. 16/687,029 filed Nov. 18, 2019, entitled "Systems and Methods to Track Cleanliness of Vehicle Exterior and Reduce Operating Expenses," which is hereby incorporated by reference herein in its entirety.

FIELD OF THE DISCLOSURE

The present disclosure relates generally to autonomous vehicles (AVs) and to systems and methods for tracking cleanliness of the exterior of a vehicle.

BACKGROUND

Autonomous vehicles, also known as self-driving cars, driverless vehicles, and robotic vehicles, are vehicles that use multiple sensors to sense the environment and move without human input. Automation technology in the autonomous vehicles enables the vehicles to drive on roadways and to accurately and quickly perceive the vehicle's environment, including obstacles, signs, and traffic lights. The vehicles can be used to pick up passengers and drive the passengers to selected destinations. Over time and with use, vehicles become dirty, and a lack of cleanliness of the vehicle can be undesirable to passengers, who prefer to ride in a clean vehicle.

SUMMARY

Systems and methods are provided for dynamically tracking the cleanliness of a vehicle's exterior. In particular, a dynamic strategy for cleaning vehicles is provided. In a system including a fleet of vehicles, the vehicles are regularly cleaned to remove dirt, dust, and any other matter that has stuck to the vehicle.

According to one aspect, a method for dynamically scheduling cleaning of the exterior of a vehicle includes measuring airborne particles with an airborne particle sensor and collecting airborne particle measurement data, determining total exposure of the vehicle to airborne particles based on the airborne particle measurement data over a first time window, determining, based in part on the total exposure, a level of cleanliness of the vehicle at the end of the first time window, and determining, based on the level of cleanliness, whether to schedule a cleaning for the vehicle. In various examples, the level of cleanliness includes the level of cleanliness of an exterior of the vehicle.

In some implementations, the method further includes scheduling the cleaning for the vehicle, wherein scheduling the cleaning depends in part on expected traffic patterns. In some implementations, the method further includes scheduling the cleaning for the vehicle, wherein scheduling the cleaning depends in part on expected weather. For example, if rain is expected, a cleaning may be delayed. In some implementations, the method further includes determining exposure of the vehicle to rain, and determining a level of cleanliness is based in part on the exposure of the vehicle to rain.

In some implementations, measuring airborne particle data includes continuously measuring airborne particle data. In other implementations, measuring airborne particle data includes intermittently measuring airborne particle data. In some implementations, the method includes accumulating airborne particle data measurements over one or more additional time windows and adding the measurements to the total exposure to yield an updated total exposure, and determining, based in part on the updated total exposure, the level of cleanliness of the vehicle at the end of the additional time windows. In some examples, the method further includes cleaning the vehicle, and wherein the total exposure and the updated total exposure are reset after the cleaning.

In some implementations, the method includes recording locations of airborne particle measurements. In some examples, the method further includes updating a mapping database with airborne particle data at the recorded locations. For example, the locations may be geographical locations as will be described in greater detail herein.

In some implementations, measuring airborne particles with an airborne particle sensor includes one of measuring particles with light scattering techniques, measuring particles with direct imaging techniques, and measuring particles with light obscuration techniques.

According to another aspect, a system for dynamically scheduling cleaning of a vehicle includes at least one sensor for measuring airborne particles, a database for collecting airborne particle measurement data, and a processor for determining total exposure of the vehicle to airborne particles based on the airborne particle measurement data, determining a level of cleanliness of the vehicle, and flagging the vehicle for cleaning when the level of cleanliness exceeds a predetermined threshold.

In some implementations, the system includes a scheduler for scheduling the vehicle for cleaning when the vehicle is flagged for cleaning. In some implementations, the at least one sensor is an optical sensor including a light source and a photosensor, and wherein the photosensor has one of fixed sensitivity and adjustable sensitivity. In some implementations, the system includes a locator for determining vehicle location, and wherein the database includes the vehicle location for each airborne particle measurement. In various examples, the locator includes a simultaneous localization and mapping system that determines the autonomous vehicle's location based on comparing sensor data to a high-density point cloud map. In some examples, the locator includes a GPS (Global Positioning System) to help determine location. In some examples, the locator includes a Global Navigation Satellite System (GNSS) to help determine location. In further examples, any location-determination technology can be used in the locator.

In some implementations, the at least one sensor for measuring airborne particles is located in a sensor suite comprising multiple types of sensors. In some implementations, the at least one sensor is located at one of the front of the vehicle, the back of the vehicle, and a side of the vehicle. In some implementations, the system includes a plurality of sensors, and the sensors are positioned at a plurality of locations on the vehicle.

According to another aspect, a method for dynamically scheduling cleanings of vehicles in a fleet of vehicles includes measuring airborne particles with an airborne particle sensor and collecting airborne particle measurement data for each of the vehicles, determining total exposure of each of the vehicles to airborne particles based on the airborne particle measurement data over a first time window, determining for each vehicle, based in part on the total exposure, a level of cleanliness of each vehicle at the end of the first time window, and determining for each vehicle, based on the level of cleanliness, whether to schedule a cleaning for the vehicle.

In some implementations, the method includes recording location information for the collected airborne particle measurement data for each vehicle, and saving recorded airborne particle measurement data for each location to a central mapping database.

BRIEF DESCRIPTION OF THE DRAWINGS

To provide a more complete understanding of the present disclosure and features and advantages thereof, reference is made to the following description, taken in conjunction with the accompanying figures, wherein like reference numerals represent like parts, in which.

DETAILED DESCRIPTION

Systems and methods are provided for dynamically tracking the cleanliness of a vehicle's exterior. In particular, a dynamic strategy for cleaning vehicles is provided. In a system including a fleet of vehicles, the vehicles are regularly cleaned to remove dirt, dust, and any other matter that has stuck to the vehicle. Traditionally, the vehicles are cleaned regularly on a set schedule or when a human manually sees that the vehicle needs cleaning. However, the vehicles may not need cleaning at the scheduled time or there may be no human operator. Cleaning a vehicle removes the vehicle from operation for the duration of the cleaning. When a vehicle is removed from operation, that vehicle is not creating revenue. Thus, systems and methods are needed to optimize vehicle cleaning schedules, such that removal of vehicles from operation is minimized.

In various implementations, a vehicle is equipped with a sensor to detect airborne particles. The sensor provides information about the cleanliness of environment through which the vehicle is travelling. In particular, the sensor provides information about airborne particles such as dirt and dust through which the vehicle is travelling. When a vehicle travels through environments with high levels of airborne particles, such as dirty or dusty environments, the vehicle becomes dirtier than when the vehicle travels through environments with lower levels of airborne particles. Over time, the dirt or dust the vehicle is exposed to accumulates on the exterior of the vehicle. As particles accumulate on the exterior of the vehicle, the vehicle becomes dirtier. According to various implementations, measurements of a vehicle's exposure to dust and dirt is used to dynamically track vehicle cleanliness. Since it is desirable to maintain a clean vehicle exterior while minimizing downtime of the vehicle, vehicle cleanliness information can be used to dynamically schedule vehicle cleanings on an as-needed basis. In particular, using information about vehicle exposure to airborne particles such as dirt and dust, vehicles can be scheduled for cleanings when the vehicles are expected to be dirty.

Figure 1A:
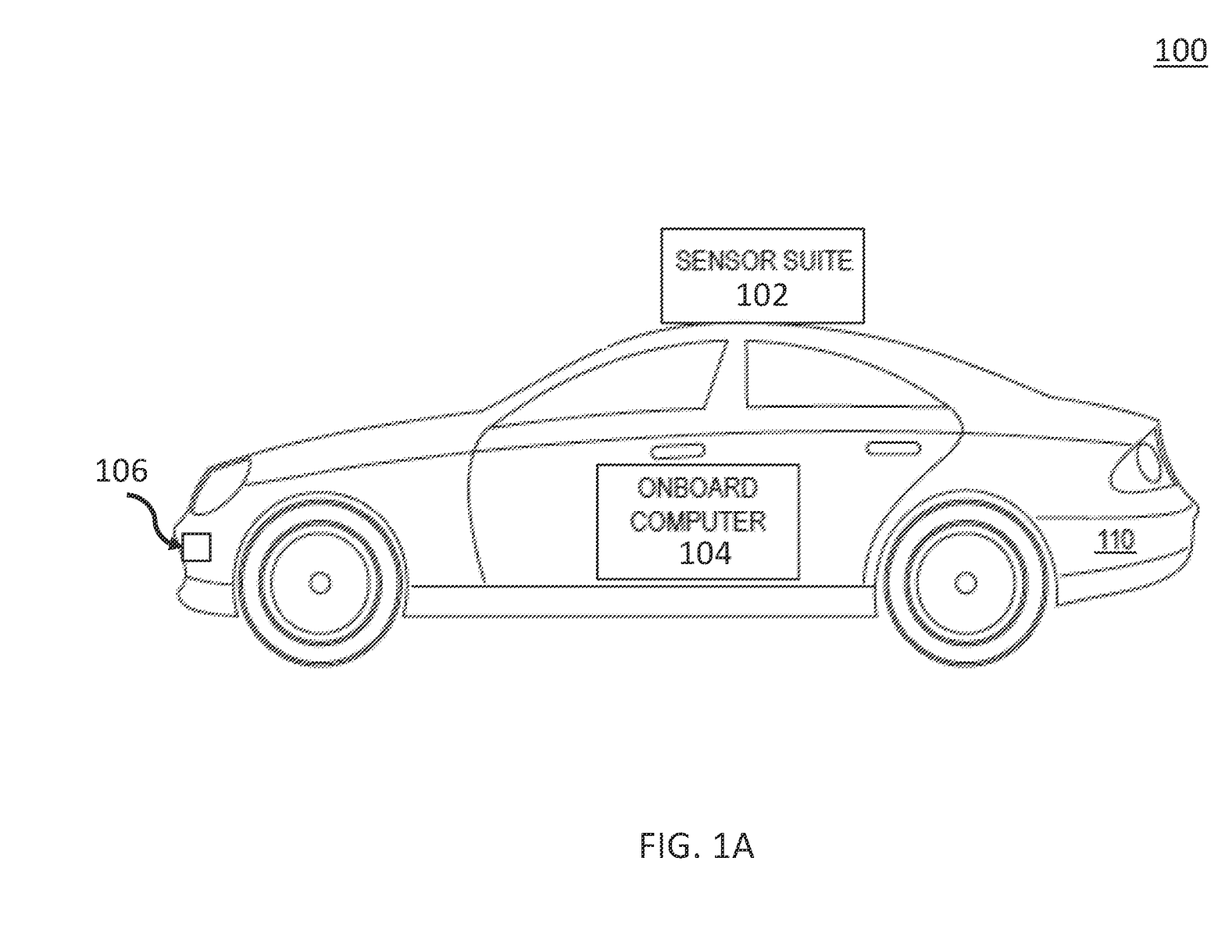
FIG. 1A is a diagram illustrating a side view of an autonomous vehicle, according to some embodiments of the disclosure.

FIG. 1A is a diagram 100 illustrating an autonomous vehicle 110, according to some embodiments of the disclosure. The autonomous vehicle 110 includes a sensor suite 102, an onboard computer 104, and an airborne particle sensor 106. In various implementations, the autonomous vehicle 110 uses sensor information from the sensor suite 102 to determine its location, to navigate traffic, and to sense and avoid various obstacles. In various examples, the sensor suite 102 includes a locator to determine vehicle location. In some implementations, the locator includes a simultaneous localization and mapping system that determines the autonomous vehicle's location based on comparing sensor data to a high-density point cloud map. In some examples, the locator includes a GPS (Global Positioning System) for location determination. In some examples, the locator includes a Global Navigation Satellite System (GNSS) for location determination. In further examples, any location-determination technology can be used in the locator, and in many examples, multiple technologies are used to determine autonomous vehicle location.

The sensor suite 102 includes localization and driving sensors. For example, the sensor suite may include one or more of photodetectors, cameras, RADAR, SONAR, LIDAR, GPS, inertial measurement units (IMUs), accelerometers, microphones, strain gauges, pressure monitors, barometers, thermometers, altimeters, wheel speed sensors, and a computer vision system. In some implementations, the sensor suite 102 includes one or more airborne particle sensors.

The airborne particle sensor 106 detects airborne particles such as dirt, dust, pollen, smoke particles, and other particles. The airborne particle sensor 106 determines the number of airborne particles present in the ambient air, as discussed in more detail with reference to FIG. 2. In some examples, the particle sensor 106 also determines the size of the detected airborne particles. In various examples, the particle sensor 106 detects particles as small as about 1 nanometer in diameter, about 2 nm in diameter, about 5 nm in diameter, or about 10 nm in diameter. In other examples the particle sensor 106 detects particles as small as about 1 micrometer in diameter. In some implementations, the sensitivity of the particle sensor 106 is adjustable, and the sensitivity may be selected by a user or determined by a computer system.

The particle sensor 106 continuously monitors airborne particles overtime. In some examples, the particle sensor 106 continuously accumulates airborne particle information over short windows of time. In some examples, the particle sensor 106 intermittently accumulates airborne particle information over short windows of time. In one example, the particle sensor 106 measures airborne particles detected over one second, saves the information, repeats the measurement for the next second, etc. The airborne particle information over time is saved and can be used to determine the exposure of the car to airborne particles over time. For example, the airborne particle information can be used to determine hourly and/or daily and/or weekly exposure of the autonomous vehicle to airborne particles. In some examples, the information about the exposure of the autonomous vehicle to airborne particle is used to determine a level of vehicle cleanliness. In some examples, the information about the exposure of the autonomous vehicle to airborne particle is used to schedule vehicle cleanings. In some implementations, the airborne particle information includes the location of each measurement.

In some implementations, the airborne particle data is stored locally in the autonomous vehicle onboard computer 104. In some implementations, the airborne particle data is transmitted to the cloud. In some implementations, the airborne particle data is transmitted to a central database and/or a central computer. The central database may store airborne particle information for multiple vehicles.

In various implementations, the autonomous vehicle 110 may include more than one airborne particle sensor 106. Furthermore, the particle sensor 106 can be placed in any location on the autonomous vehicle 110.

Figure 1B:
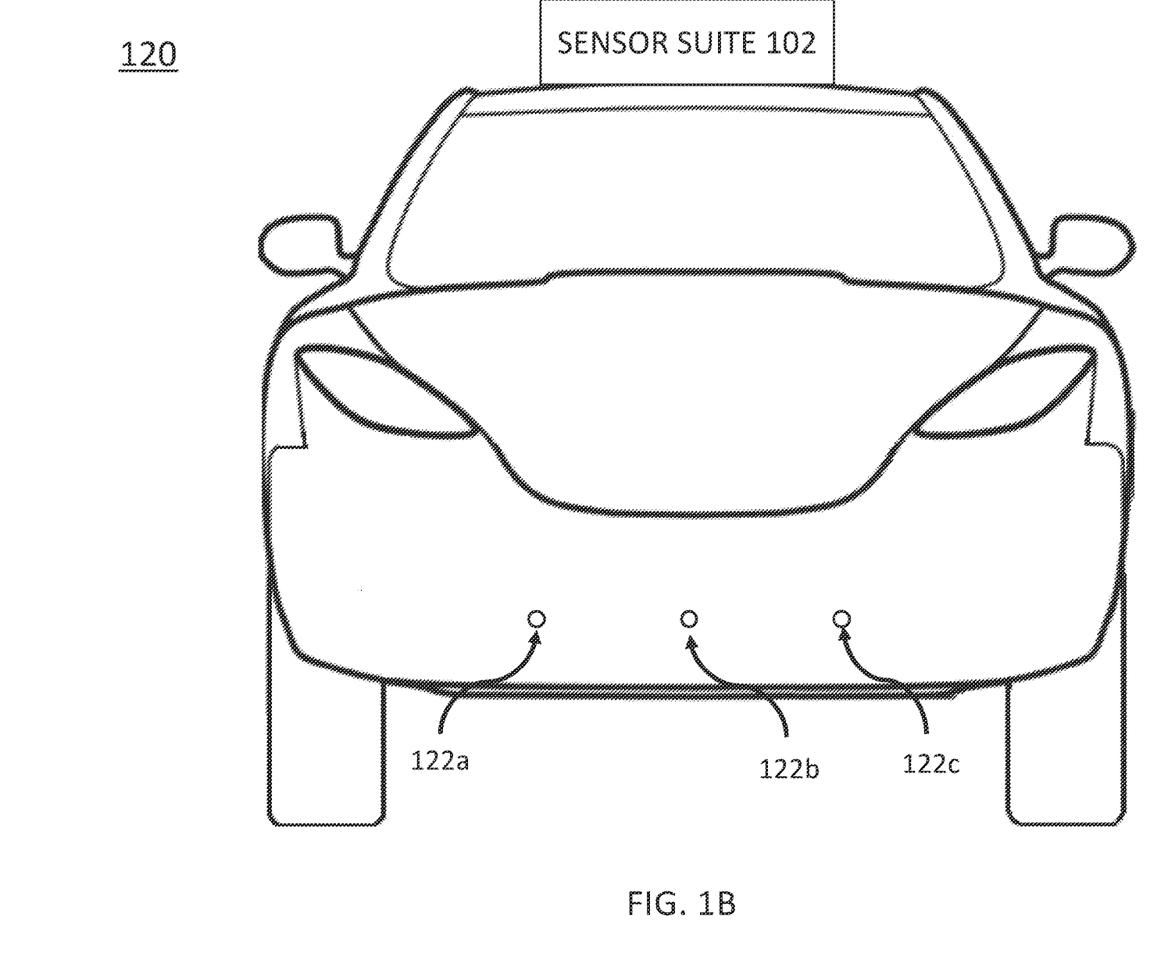
FIG. 1B is a diagram illustrating a front view of an autonomous vehicle, according to some embodiments of the disclosure.

FIG. 1B is a diagram illustrating a front view 120 of an autonomous vehicle 110, according to some embodiments of the disclosure. The front view 120 shows an implementation in which first 122a, second 122b, and third 122c airborne particle sensors are placed on the front of the vehicle 110. The first 122a, second 122b, and third 122c airborne particle sensors may be placed below, within, or above the vehicle's bumper.

In some implementations, airborne particle sensors are placed in multiple locations on the vehicle, including, for example, on one or both sides of the vehicle, and/or at the back of the vehicle. The airborne particle sensors may be placed higher up on the vehicle and/or lower down on the vehicle. In some examples, airborne particle data may be different depending on where the airborne particle sensor is placed on the vehicle.

In various examples, the sensor suite 102 includes cameras implemented using high-resolution imagers with fixed mounting and field of view. In further examples, the sensor suite 102 includes LIDARs implemented using scanning LIDARs. Scanning LIDARs have a dynamically configurable field of view that provides a point-cloud of the region intended to scan. In still further examples, the sensor suite 102 includes RADARs implemented using scanning RADARs with dynamically configurable field of view.

The autonomous vehicle 110 includes an onboard computer 104, which functions to control the autonomous vehicle 110. The onboard computer 104 processes sensed data from the sensor suite 102 and/or other sensors, such as the airborne particle sensor 106, in order to determine a state of the autonomous vehicle 110. Based upon the vehicle state and programmed instructions, the onboard computer 104 controls and/or modifies driving behavior of the autonomous vehicle 110.

The onboard computer 104 functions to control the operations and functionality of the autonomous vehicles 110 and processes sensed data from the sensor suite 102 and/or other sensors in order to determine states of the autonomous vehicles. The onboard computer 104 is preferably a general-purpose computer adapted for I/O communication with vehicle control systems and sensor systems, but may additionally or alternatively be any suitable computing device. The onboard computer 104 is preferably connected to the Internet via a wireless connection (e.g., via a cellular data connection). Additionally or alternatively, the onboard computer 104 may be coupled to any number of wireless or wired communication systems. In some examples, the onboard computer 104 is coupled to one or more communication systems via a mesh network of devices, such as a mesh network formed by autonomous vehicles.

According to various implementations, the autonomous driving system 100 of FIG. 1 functions to enable an autonomous vehicle 110 to modify and/or set a driving behavior in response to parameters set by vehicle passengers (e.g., via a passenger interface) and/or other interested parties (e.g., via a vehicle coordinator or a remote expert interface). Driving behavior of an autonomous vehicle may be modified according to explicit input or feedback (e.g., a passenger specifying a maximum speed or a relative comfort level), implicit input or feedback (e.g., a passenger's heart rate), or any other suitable data or manner of communicating driving behavior preferences.

The autonomous vehicle 110 is preferably a fully autonomous automobile, but may additionally or alternatively be any semi-autonomous or fully autonomous vehicle. In various examples, the autonomous vehicle 110 is a boat, an unmanned aerial vehicle, a driverless car, a golf cart, a truck, a van, a recreational vehicle, a train, a tram, a three-wheeled vehicle, or a scooter. Additionally, or alternatively, the autonomous vehicles may be vehicles that switch between a semi-autonomous state and a fully autonomous state and thus, some autonomous vehicles may have attributes of both a semi-autonomous vehicle and a fully autonomous vehicle depending on the state of the vehicle.

In various implementations, the autonomous vehicle 110 includes a throttle interface that controls an engine throttle, motor speed (e.g., rotational speed of electric motor), or any other movement-enabling mechanism. In various implementations, the autonomous vehicle 110 includes a brake interface that controls brakes of the autonomous vehicle 110 and controls any other movement-retarding mechanism of the autonomous vehicle 110. In various implementations, the autonomous vehicle 110 includes a steering interface that controls steering of the autonomous vehicle 110. In one example, the steering interface changes the angle of wheels of the autonomous vehicle. The autonomous vehicle 110 may additionally or alternatively include interfaces for control of any other vehicle functions, for example, windshield wipers, headlights, turn indicators, air conditioning, etc.

As described herein, one aspect of the present technology is the gathering and use of data available from various sources to improve quality and experience. The present disclosure contemplates that in some instances, this gathered data may include personal information. The present disclosure contemplates that the entities involved with such personal information respect and value privacy policies and practices.

Figure 2:
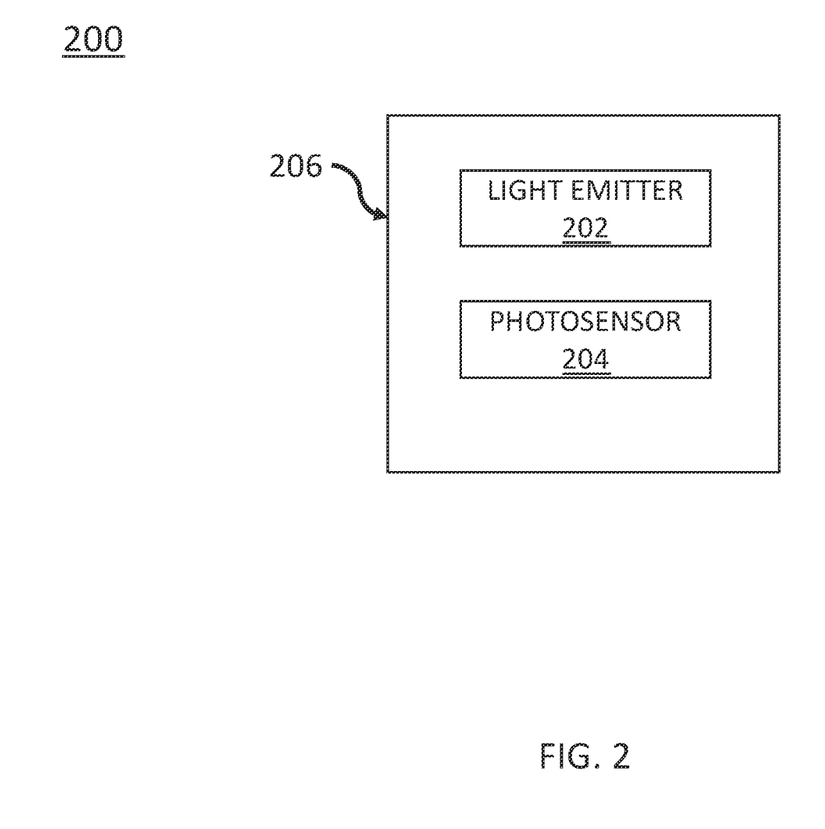
FIG. 2 is a diagram illustrating a particle sensor, according to some embodiments of the disclosure.

FIG. 2 is a diagram 200 illustrating a particle sensor 206, according to some embodiments of the disclosure. The particle sensor 206 includes a light emitter 202 and a photo-sensor 204. The particle sensor 206 uses an optical sensing method to detect particles in the air. The light emitter 202 emits light into the environment and the photosensor 204 detects any light reflected back. In particular, when the emitted light reflects off a particle in the air, the photosensor 204 detects the reflected light. Measurements of reflected light are used to determine an amount of airborne particles. In one example, the light emitter 202 is a light emitting diode (LED), and in a particular example, the LED is an infrared LED.

In some implementations, the particle sensor 206 includes a detection chamber. The light source is directed into the detection chamber, and particles in the air passing through the detection chamber are detected by a photo detector. Various methods can be used for airborne particle detection. In some examples, airborne particle detection is based on light scattering. In some examples, airborne particle detection is based on direct imaging. In some examples, airborne particle detection is based on light obscuration or light extinction. In various implementations, the light source is one of a laser light source, a halogen light source, and a LED. The light source emits high intensity light. With light scattering, when particles in the air in the detection chamber pass through the light source, the redirected light is detected by the photodetector. In direct imaging, when particles in the air in the detection chamber pass through the light source, the particles are illuminated from the back and a high definition camera records airborne particles. Computer software analyzes the recorded data to determine particle count and measure particle attributes. In light obscuration, the loss of light due to the presence of particles is detected. The amplitude of light scattered or blocked is measured to detect airborne particles and determine airborne particle concentration.

In another implementation, the airborne particle sensor 206 is an optical-fiber-based sensor. An optical-fiber-based sensor detects the particle through the drop in optical fiber coupling efficiency as the particle disrupts the electromagnetics of the optical beam.

In various implementations, various types of airborne particle sensors are used on the autonomous vehicle. In other examples, a single type of airborne particle sensor is used on the autonomous vehicle.

In some implementations, the photosensor 204 has a fixed sensitivity. In other implementations, the photosensor 204 has an adjustable sensitivity. In a photosensor with an adjustable sensitivity, the sensitivity can be set by a user, by the onboard computer 104, by a central computer system, or by an autonomous vehicle fleet manager. According to various examples, the photosensor 204 sensitivity is set to detect particles as small as about 10 nanometers in diameter, about 25 nanometers in diameter, about 50 nanometers in diameter, about 100 nanometers in diameter, about 1 micrometer in diameter, or about 5 micrometers in diameter. In various examples, cigarette smoke particle size is about one micrometer, and dust particle size is about 20 micrometers.

According to various implementations, the particle sensor 206 can distinguish between particles of different sizes by using various pulse patterns for the light emitted from the light emitter. For example, the particle sensor 206 can distinguish between small particles of dirt or dust and large particles of dirt or dust. In some examples, the particle sensor 206 uses pulse width modulation (PWM) output for particle detection, and has a low pulse output. In some examples, using PWM, pulse width is proportional to particle size concentration.

The particle sensor 206 is a small sensor, measuring less than about 1 square centimeter in size. In one example, the particle sensor 206 is less than about 0.5 cm in size. In another example, the particle sensor 206 is rectangular, and has a width that is less than about 1 cm, a height that is less than about 0.5 cm, and a depth that is less than about 0.2 cm. In various implementations, the particle sensor 206 weight less than about 50 grams, less than about 25 grams, or less than about 20 grams.

Figure 3:
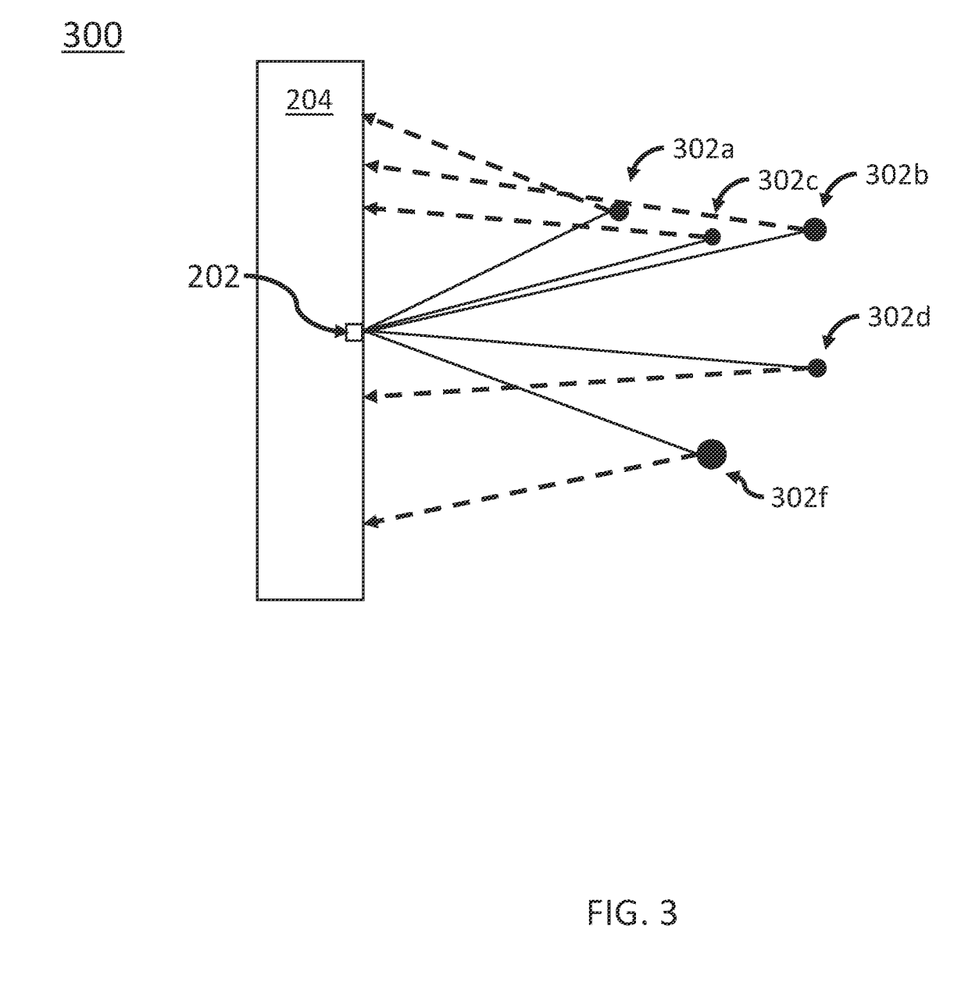
FIG. 3 is a diagram illustrating a particle sensor emitting light, according to some embodiments of the disclosure.

FIG. 3 is a diagram 300 illustrating a particle sensor emitting light, according to some embodiments of the disclosure. The particle sensor includes the light emitter 202 and the photodetector 204. The light emitter 202 emits light, and, as shown in the diagram 300, the light hits various airborne particles 302a, 302b, 302c, 302d, and 302e, and either scatters to or reflects back to the photodetector 204.

Figure 4:
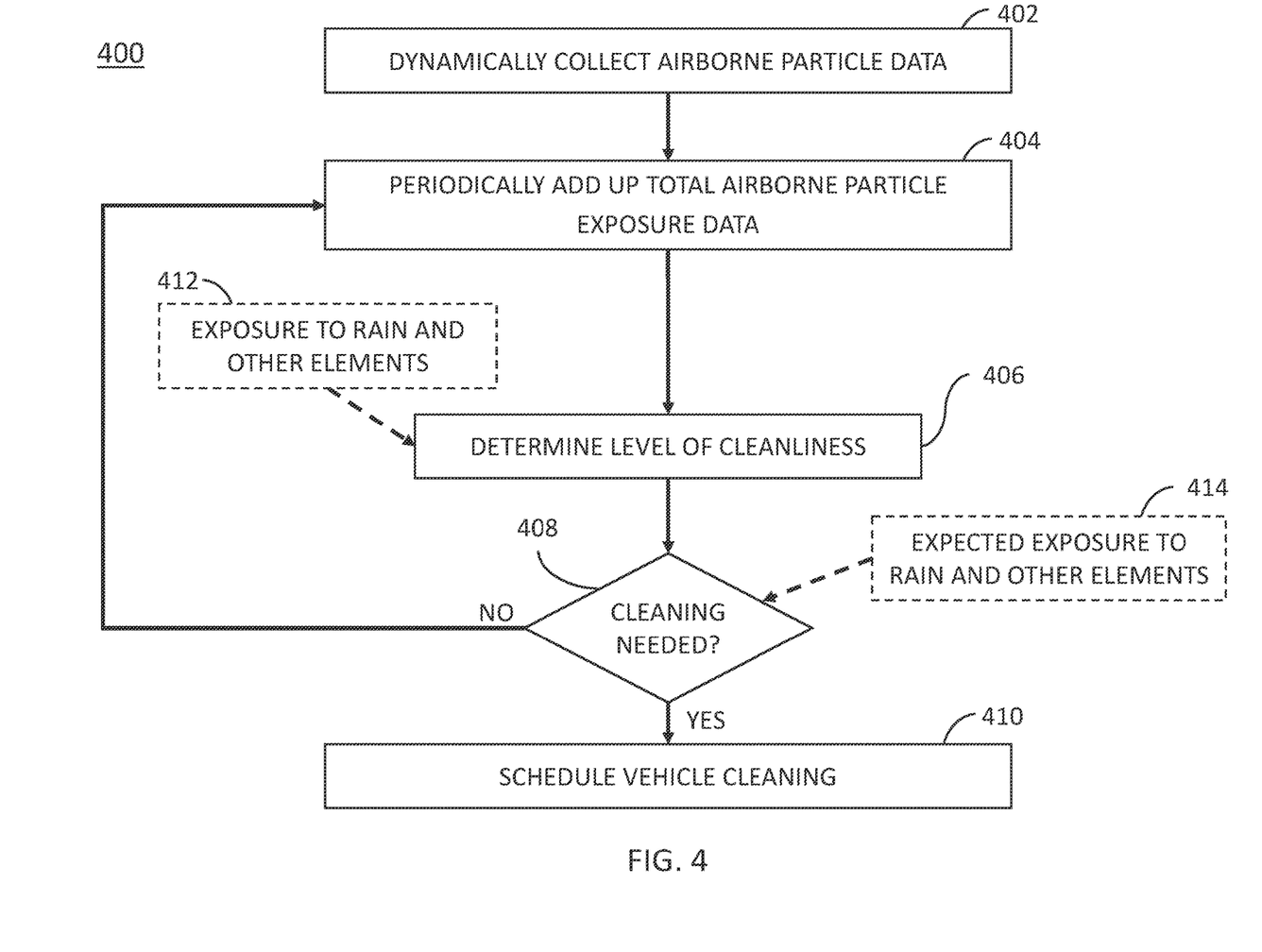
FIG. 4 a flow chart illustrating a method of dynamically tracking the cleanliness of a vehicle, according to some embodiments of the disclosure.

FIG. 4 a flow chart illustrating a method 400 of dynamically tracking the cleanliness of a vehicle and scheduling vehicle cleanings, according to some embodiments of the disclosure. At step 402, airborne particle information is dynamically collected. As described above, sensors on the vehicle monitor airborne particle information. In some examples, the airborne particle information is continuously collected. In other examples, the airborne particle information is intermittently collected. At step 404, the collected airborne particle information is periodically summed to result in a total amount of exposure.

At step 406, a level of cleanliness of the vehicle is determined, based in part on the total amount of exposure of the vehicle to airborne particles. Other data may also be used to determine of the level of cleanliness. At step 412, exposure of the vehicle to rain and other elements can be determined and factored into the cleanliness determination at step 406. For example, exposure of the vehicle to rain may increase the level of cleanliness (as some dirt, dust, and other airborne particles will have been washed off), while exposure to snow may decrease the level of cleanliness (because of road salt, sand, and other elements that tend to dirty the vehicle).

At step 408, the method 400 determines whether the vehicle needs cleaning. For example, the method 400 may determine whether the vehicle needs cleaning if determined that the level of cleanliness exceeds a predetermined threshold. In addition to the level of cleanliness determined at step 406, other factors may be considered in determining whether a vehicle needs to be cleaned. For example, at step 414, expected exposure of the vehicle to rain and other weather may be considered. In one example, if a heavy downpour is expected, a cleaning may be delayed with the expectation that the expected rain will clean some of the dirt and dust off the vehicle. Similarly, in another example, if snow is expected, a cleaning may be delayed due to an expectation that the expected weather conditions will result in the vehicle becoming much dirtier and the cleaning may be delayed until after the snow. At step 408, if it is determined that no cleaning is warranted, the method returns to step 404 and continues to accumulate total airborne particle exposure data. If, at step 408, it is determined that a cleaning is needed, the method proceeds to step 410 and a vehicle cleaning is scheduled. After a vehicle is cleaned, the total airborne particle exposure data is reset to zero.

In some implementations, the method 400 is performed locally, in the onboard computer of the vehicle. In other implementations, data from the vehicle is transmitted to a computing cloud, and the method 400 is performed at an off-site processing center.

According to various implementations, scheduling of the vehicle cleaning considers other factors, in addition to the level of cleanliness and expected exposure to rain and other elements. In one example, the scheduling considers the number of vehicles in the fleet that need cleaning, and cleanings are scheduled to minimize the number of vehicles that are out of service for cleanings at any given time. In another example, the scheduling considers other services the vehicle needs and schedules the cleanings to coincide with when the vehicle is at a service center. In another example, the scheduling considers vehicle location, and schedules the cleaning for a time when the vehicle is close to the cleaning service center. In some examples, some examples, the scheduling of the vehicle cleaning is correlated with customer demand. In particular, vehicles are more likely to be scheduled for a cleaning when customer demand is low. Similarly, when fewer vehicles are scheduled for cleanings when customer demand is high.

According to some implementations, mapping vehicles collect airborne particle information. In some examples, certain autonomous vehicles are dedicated to mapping selected areas. Mapping includes mapping of streets and also updating maps based on construction, traffic congestion at various times of day, and timing to traverse selected routes. In some implementations, mapping information includes airborne particle data at various locations, and mapping vehicles collect data on airborne particle concentrations. In some examples, this data is used to avoid routing vehicles through dirty/dusty areas (areas with high airborne particle concentrations) in order to keep vehicles cleaner for longer stretches of time. In some examples, when vehicles are waiting on the road for a next request during a low demand period, airborne particle data is considered in selecting the waiting area for the vehicle. In particular, a waiting vehicle can be routed to wait in an area with low airborne particle count, indicating an area with low levels of dirt and dust. It is to be understood that airborne particle information and other mapping information may be collected by other types of autonomous vehicles and used in the same way.

Figure 5:
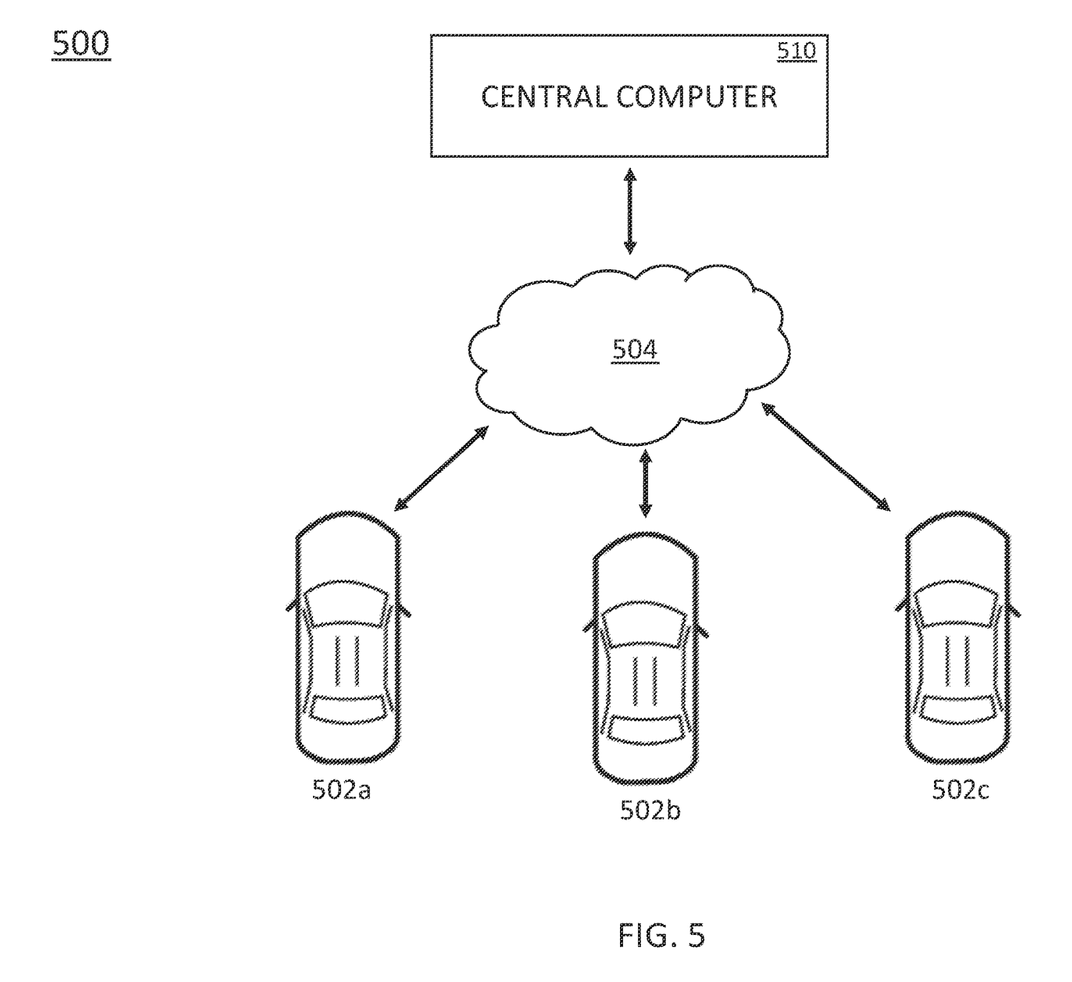
FIG. 5 is a diagram illustrating a fleet of vehicles in communication with a central computer according to some embodiments of the disclosure.

FIG. 5 is a diagram 500 illustrating a fleet of vehicles 502a, 502b, 502c in communication with a central computer 510, according to some embodiments of the disclosure. As shown in FIG. 5, the vehicles 502a, 502b, 502c communicate wirelessly to a cloud 504 and a central computer 510. The central computer 510 includes a database of information from the vehicles in the fleet and a routing coordinator. Autonomous vehicle fleet routing refers to the routing of multiple vehicles in a fleet. In some implementations, autonomous vehicles communicate directly with each other.

Each vehicle in the fleet of vehicles communicates with a routing coordinator. Information gathered by various autonomous vehicles in the fleet can be saved and used to generate information for future routing determinations. For examples, sensor data can be used to generate route determination parameters. In general, the information collected from the vehicles in the fleet can be used for route generation or to modify existing routes. In some examples, the routing coordinator collects and processes position data from multiple autonomous vehicles in real-time to avoid traffic and generate a fastest-time route for each autonomous vehicle. In some implementations, the routing coordinator uses collected position data to generate a best route for an autonomous vehicle in view of one or more travelling preferences and/or routing goals. In some examples, the routing coordinator uses airborne particle data to avoid particularly dirty and/or dusty areas.

According to various implementations, a set of parameters can be established that determine which metrics are considered (and to what extent) in determining routes or route modifications. Generally, a routing goal refers to, but is not limited to, one or more desired attributes of a routing plan indicated by at least one of an administrator of a routing server and a user of the autonomous vehicle. The desired attributes may relate to a desired duration of a route plan, a comfort level of the route plan, a vehicle type for a route plan, and the like. For example, a routing goal may include time of an individual trip for an individual autonomous vehicle be minimized, subject to other constraints. As another example, a routing goal may be that comfort of an individual trip for an autonomous vehicle be enhanced or maximized, subject to other constraints.

Routing goals may be specific or general in terms of both the vehicles they are applied to and over what timeframe they are applied. As an example of routing goad specificity in vehicles, a routing goal may apply only to a specific vehicle, or to all vehicles in a specific region, or to all vehicles of a specific type, etc, Routing goal timeframe may affect both when the goal is applied (e.g., some goals may be 'active' only during set times) and how the goal is evaluated (e.g., for a longer-term goat, it may be acceptable to make some decisions that do not optimize for the goal in the short term, but may aid the goal in the long term). Likewise, routing vehicle specificity may also affect how the goal is evaluated; e.g., decisions not optimizing for a goal may be acceptable for some vehicles if the decisions aid optimization of the goal across an entire fleet of vehicles.

Some examples of routing goals include goals involving trip duration (either per trip, or average trip duration across some set of vehicles and/or times), physics, laws, and/or company policies (e.g., adjusting routes chosen by users that end in lakes or the middle of intersections, refusing to take routes on highways, etc.), distance, velocity (e.g., max., min., average), source/destination (e.g., it may be optimal for vehicles to start/end up in a certain place such as in a pre-approved parking space or charging station), intended arrival time (e.g., when a user wants to arrive at a destination), duty cycle (e.g., how often a car is on an active trip vs. idle), energy consumption (e.g., gasoline or electrical energy), maintenance cost (e.g., estimated wear and tear), money earned (e.g., for vehicles used for ridesharing), person-distance (e.g., the number of people moved multiplied by the distance moved), occupancy percentage, higher confidence of arrival time, user-defined routes or waypoints, fuel status (e.g., how charged a battery is, how much gas is in the tank), passenger satisfaction (e.g., meeting goals set by or set for a passenger) or comfort goals, environmental impact, passenger safety, pedestrian safety, toll cost, etc. In examples where vehicle demand is important, routing goals may include attempting to address or meet vehicle demand.

With respect to routing goals relating to comfort and/or passenger satisfaction, these type of routing goals may include a number of passenger or routing coordinator instructions for improving a level of comfort of a ride in an autonomous vehicle. Accordingly, an aim of enhancing comfort of a ride in an autonomous vehicle is to mitigate or reduce maneuvers or segments of a ride that contribute negatively to an ease of a ride including one or more uneasy sensations that may be experienced by a passenger during the ride. Examples of comfort metrics or attributes of a ride that may contribute negatively to comfort include multiple lane changes, curvature of a lane or road, minor/major and major/minor turns, unprotected lefts, zipper mergers, curvature of road that makes turns uncomfortable or jerk too high, number of turns in a path, destinations having an ability to pull over, and the like. These metrics or attributes of a ride in an autonomous vehicle can be minimized or in some cases, increased depending on preferences.

Routing goals may be combined in any manner to form composite routing goals; for example, a composite routing goal may attempt to optimize a performance metric that takes as input trip duration, rideshare revenue, and energy usage and also, optimize a comfort metric. The components or inputs of a composite routing goal may be weighted differently and based on one or more routing coordinator directives and/or passenger preferences.

Likewise, routing goals may be prioritized or weighted in any manner. For example, a set of routing goals may be prioritized in one environment, while another set may be prioritized in a second environment. As a second example, a set of routing goals may be prioritized until the set reaches threshold values, after which point a second set of routing goals take priority. Avoiding dirty or dusty areas may be a routing goal. Routing goals and routing goal priorities may be set by any suitable source (e.g., an autonomous vehicle routing platform, an autonomous vehicle passenger).

In various implementations, autonomous vehicles in a fleet of vehicles both provide and receive airborne particle information. In particular, autonomous vehicle measure current airborne particle data and transmit the data to a central processor as described above, and autonomous vehicles also receive routing information that includes airborne particle data. In one example, a first autonomous vehicle receives route information based in part on sensor data provided by a second autonomous vehicle travelling separately from the first autonomous vehicle. In this example, the first autonomous vehicle is both a recipient of routing instructions based in part on airborne sensor data from the second autonomous vehicle, and the first autonomous vehicle is also a donor of sensor data. In various implementations, when a vehicle is flagged for cleaning, and a cleaning is scheduled, the routing coordinator determines a route for the vehicle to the service center for cleaning.

In various implementations, the routing coordinator is a remote server or a distributed computing system connected to the autonomous vehicles via an internet connection. In some implementations, the routing coordinator is any suitable computing system. In some examples, the routing coordinator is a collection of autonomous vehicle computers working as a distributed system.

In some implementations, a route is modified based on route modification parameters. Route parameters are generated to aid in the understanding of how to modify a route in response to the autonomous vehicle sensor data and/or the vehicle demand data, as we as the routing aoals in general, route modification parameters preferably link data pertaining to routing goals to a route or part of a route. Additionally or alternatively, route modification parameters may include any data that aids understanding of how a route should be modified based on received data received from the sensor suite and/or airborne particle sensors, or other data.

Route modification parameters may be linked with any characteristic that can be used to describe a route or part of a route. For example, route modification parameters may be linked with individual road sections (e.g., streets segmented by block and direction of traffic), roads, geographic regions, direction of traffic, direction of travel (e.g., relative to some landmark ora compass heading), type of road (e.g., freeway, surface road), actions on a road section or at an intersection (e.g., turns, U-turns, waiting at stoplights between road sections), and/or a set of road sections (e.g., a route or part of a route that traverses more than one road).

Route modification parameters are preferably further linked, either directly or indirectly, with routing goals (alternatively, route modification parameters may be unlinked with routing goals). For example, a route modification parameter linking a traffic or traffic delay score to a road section may be linked with a routing goal corresponding to travel time, a routing goal corresponding to energy usage, and/or a routing goal corresponding to arrival time. The link between a route modification parameter and a route or a segment of a route or the like may be established in any manner. For instance, a route modification parameter such as a blacklist parameter may be stored in association with a route segment that is prohibited from being traveled such that when the route segment is identified or selected, an indication that the route segment is blacklisted is automatically populated to a user or indicated to a routing coordinator. Additionally or alternatively, any route or route segment that has been flagged has a blacklisted route segment or blacklisted path may be stored in a table specifically for blacklisted route segments or blacklisted paths. The table may also include other sections related to other circumstances that should be avoided.

Additionally, route modification parameters such as an existence of construction on a route or route segment affecting one or more lanes or the like may also be saved. In a preferred embodiment, a predetermined three-dimensional (3D) map of a geographic region is provided or generated using LIDAR and high precision GPS. This 3D map may have been created at a previous time in the past possibly using the sensor suites from one or more autonomous vehicles or the like or possibly acquired from an external using. The predetermined 3D map of the geographic region is preferably updated to include route modification parameters such as blacklisted lanes or path, construction areas, accident sites, and the like. The predetermined 3D map may be updated in real-time or near real-time to reflect recently generated route modification parameters or updated values for route modification parameters. Thus, each of the route modification parameters may be represented on the 3D map by superimposing the route modification parameter onto the mar or the like. In the case that route generation occurs at a central authority, the 3D map is updated at the central authority (e.g., routing coordinator) and the updated 3D map is then considered in any ongoing or future route generation processes. Additionally, the updated 3D map is transmitted to all autonomous vehicles in a feet. A technical benefit of augmenting the 3D map of a geographic region with route modification parameters is that all or more route modification parameters may be viewed and additionally accessed from a single source. Thus, a global view of the traffic circumstances of an entire region may be interpreted from a single map. Additionally, processing route modification parameters in a route generation process in simplified because only a single source or database must be accessed for identifying all route modification parameters affecting a particular route, route segment, or geographic region in which a route plan is to be produced In various examples, the methods discussed herein operable by a set (or fleet) of autonomous vehicles without dedicated user interfaces or routing coordinators and/or without a central authority server. In some implementations, the fleet of autonomous vehicles collectively negotiates a route for one autonomous vehicle in the set using intelligence sensed by each of the autonomous vehicles in the set, as well as information obtained from external sources (e.g., live traffic reporting, live construction data, etc.). Partial processing of the route to be generated may occur across the fleet of autonomous vehicles and be combined for a completed generated route at the subject autonomous vehicles requiring the route. In some examples, partial processed parts of the route are assembled together at a non-subject autonomous vehicle of the fleet and then the generated route is transmitted to the subject autonomous vehicle.

Figure 6:
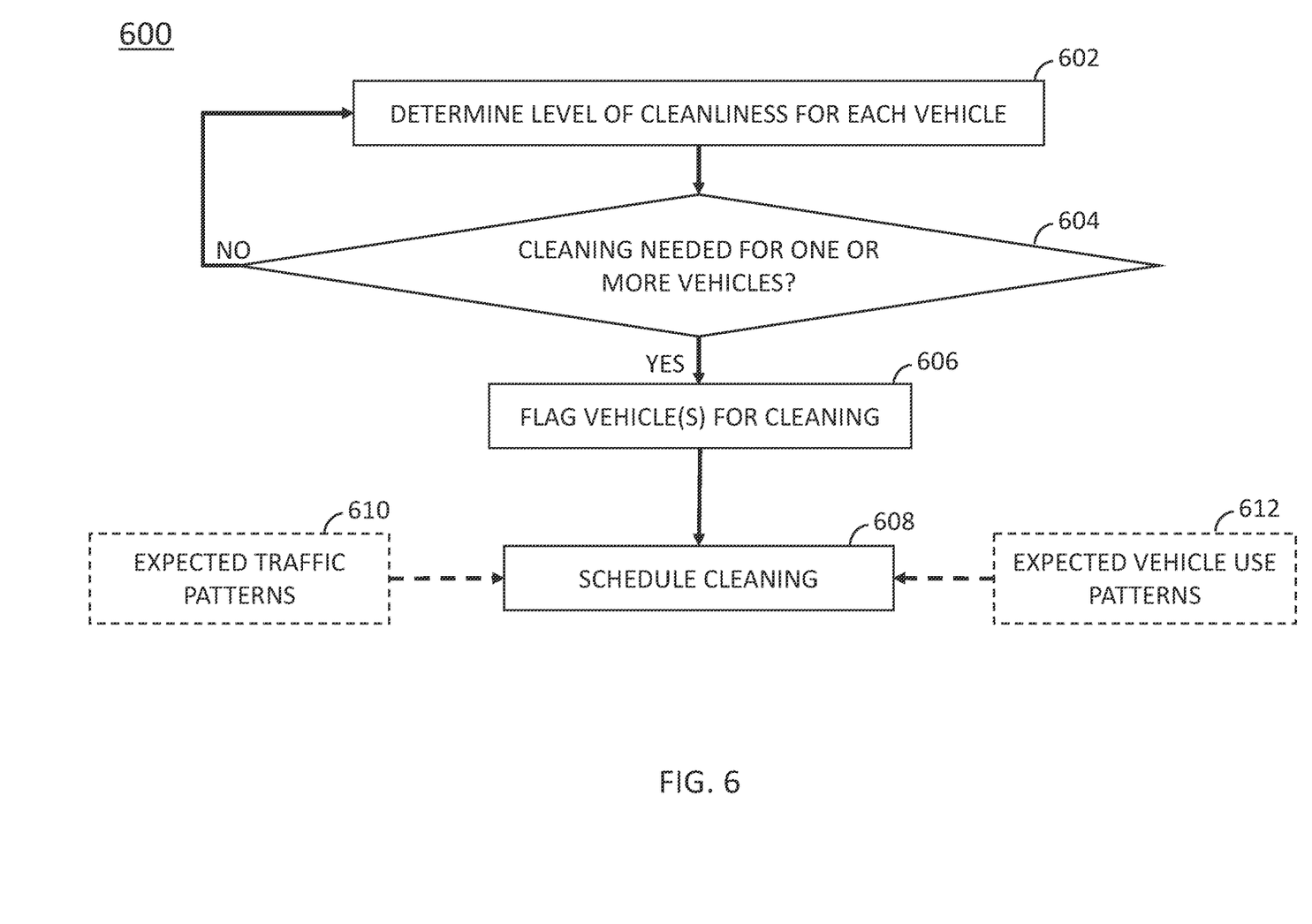
FIG. 6 is a flow chart illustrating a method of dynamically scheduling vehicle cleanings for a fleet of autonomous vehicles, according to some embodiments of the disclosure.

FIG. 6 is a flow chart illustrating a method 600 of dynamically scheduling vehicle cleanings for a fleet of autonomous vehicles, according to some embodiments of the disclosure. At step 602, a level of cleanliness is determined for each vehicle. In various examples, cleanliness level is determined at an onboard computer for each autonomous vehicle in the fleet, and each autonomous vehicle periodically transmits its cleanliness level to a central computer. In some examples, each autonomous vehicle transmits airborne particle data to a central computer, and a cleanliness level of each autonomous vehicle is determined at the central computer.

At step 604, the method determines whether cleaning is needed for one or more vehicles. If cleaning is not needed, the method 600 returns to step 602, and periodically determines the cleanliness level for each vehicle. If one or more vehicles does need cleaning (for example, if the cleanliness level of one or more vehicles exceeds a predetermined threshold cleanliness value), the one or more vehicles are flagged for cleaning at step 606.

Once one or more vehicles is flagged for cleaning at step 606, the cleaning is scheduled at step 608. Scheduling vehicle cleaning for vehicles in a fleet can take into account a number of factors. In particular, fleet scheduling considers the location and availability of each of the vehicles in the fleet, such that only a small percentage of fleet vehicles will be out of service for maintenance or cleaning at any given time. Additionally, expected traffic patterns are considered (step 610) such that the vehicle is not removed from service for cleaning at an especially busy time. In one example, a vehicle flagged for cleaning remains in service during rush hour and during a rush time period such as after an event that draws large crowds, and is removed from service for cleaning at a time period when the fleet is expected to be less busy. Furthermore, expected vehicle use patterns are considered (step 612) such that the vehicle is routed to the service center at a time when it is already relatively close to the service center.

In some implementations, expected vehicle use patterns include vehicle demand data from multiple vehicles. Vehicle demand data includes data on when, where, and what type of vehicle is needed at various times. For example, vehicle demand data includes known needs for where vehicles are needed at selected times as well as where vehicles are predicted to be needed at a future time. Vehicle demand data may include any data related to past, present, and future requests for one or more vehicles to be present in a specific area or at a specific location at specified times. In some examples, vehicle demand data includes information about the type of vehicle such as functionality, size, speed, class (luxury vs economy), or other specifications.

In some examples, expected or predicted vehicle demand data is calculated from one or more data sources linked to vehicle demand, such as historical traffic data and historical actual vehicle demand. Predicted vehicle demand data can be linked to uncontrolled variables such as weather, time of day, and data that indicate higher anticipated demand such as timing and location of concerts or sports events. Predicted vehicle demand data can also be linked to controlled variables such as the number of ridesharing vehicles available in the area and price. Controlled variables can be modified to achieve a particular predicted demand.

Figure 7:
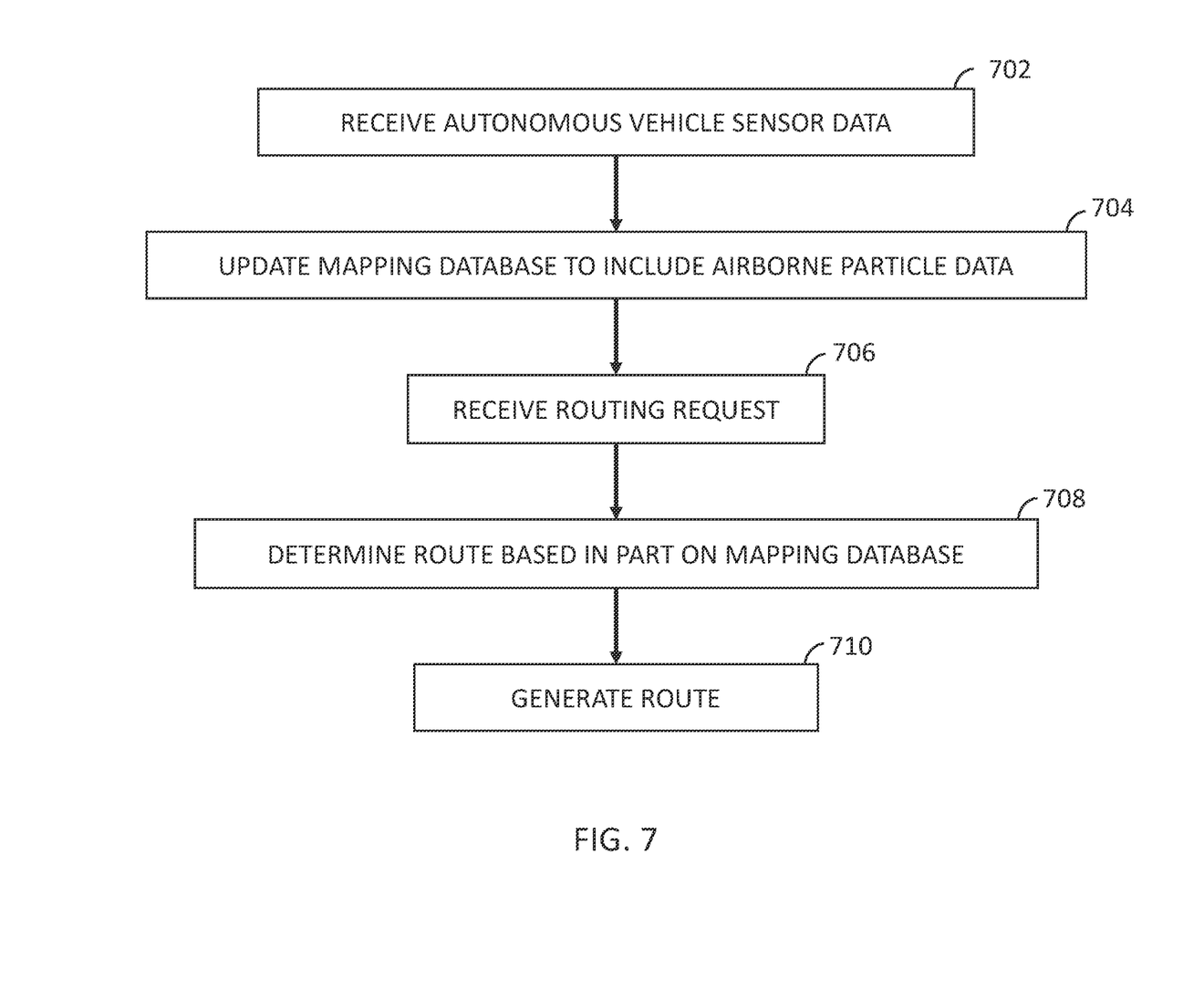
FIG. 7 is a diagram illustrating a method of adjusting vehicle mapping protocols based on airborne particle detection, according to some embodiments of the disclosure.

FIG. 7 is a diagram illustrating a method 700 of adjusting vehicle mapping protocols based on airborne particle detection, according to some embodiments of the disclosure. According to various implementations, airborne particle data can be used in fleet routing. Areas that are particularly dirty or dusty have high levels of airborne particles, and the dirtier and dustier areas cause vehicles to become dirtier. Thus, in some implementations, the areas that are mapped as having high levels airborne particles are avoided in routing vehicles. In some implementations, the areas with high levels of airborne particles are avoided when there are no passengers in the vehicle. In some instances, areas with high levels of airborne particles are not avoided. For example, when passengers are in the vehicle, selecting the fastest route is prioritized. In various implementations, parameters are assigned different levels of importance in different situations.

At step 702 of the method 700, autonomous vehicle sensor data is received. For a fleet of vehicles, autonomous vehicle sensor data is received for multiple vehicles. At step 704, a mapping database is updated to include recent airborne particle data. The mapping database includes numerous parameters for each of many locations, including street blocks, intersections, highways, and other locations. In some examples, the mapping database includes parameters for specific GPS locations. The mapping database parameters include airborne particle data for each location. According to various examples, the mapping database parameters also include information about the condition of the road or pavement at each location, any ongoing construction at each location, and traffic information at each location. In general, data gathered by autonomous vehicles in the fleet can be used for route generation or route modification for autonomous vehicles in determining routes that best meet selected criteria.

At step 706 a routing request is received from an autonomous vehicle. At step 708, the route for the vehicle is determined based in part on the parameters in the mapping database. In various examples, the parameters include airborne particle data for locations along the route. At step 710, the route is generated based on the route determination. In some implementations, steps 708 and 710 are repeated while an autonomous vehicle is en route and the route can be regenerated based on updated information.

The communication interface of each autonomous vehicle functions to allow Internet and inter-vehicle communications. For example, in many autonomous vehicles a router may form part of the communication interface. In some examples, the router is a highly reliable Wi-Fi router. The router may be modified to include multiple cellular connection/communication chips for enabling highly reliable wireless communications (e.g., Internet communications, inter-vehicle communications, etc.) between each of the autonomous vehicles and between an autonomous vehicle and one or more servers. In some examples, the router is modified to includes two, three, four, five, six, seven, eight, nine, ten, or more than ten cellular connection/communication chips. A multiplexer is formed between the four chips such that signals from the multiple cellular chips can be combined into one signal over one or more shared mediums. This allows for the distribution of work among the cellular chips to provide the highly reliable connection. In one example, the multiplexer allows for bytes of a single network packet to be divided among the cellular chips in order to simulate a single cellular chip. If any of the four cellular chips should fail for any reason, the workload of the failed chip can be re-allocated to another of the active cellular chips or distributed (re-balanced) evenly among the remaining active cellular chips thereby allowing for continuity in communication in the event that one or more of the cellular chips fail.

Variations and Implementations

According to various examples, driving behavior includes any information relating to how an autonomous vehicle drives. For example, driving behavior includes how and when the autonomous vehicle actuates its brakes and its accelerator, and how it steers. In particular, the autonomous vehicle is given a set of instructions (e.g., a route or plan), and the driving behavior determines how the set of instructions is implemented to drive the car to and from various destinations, and, potentially, to stop for passengers or items. Driving behavior may include a description of a controlled operation and movement of an autonomous vehicle and the manner in which the autonomous vehicle applies traffic rules during one or more driving sessions. Driving behavior may additionally or alternatively include any information about how an autonomous vehicle calculates routes (e.g., prioritizing fastest time vs. shortest distance), other autonomous vehicle actuation behavior (e.g., actuation of lights, windshield wipers, traction control settings, etc.) and/or how an autonomous vehicle responds to environmental stimulus (e.g., how an autonomous vehicle behaves if it is raining, or if an animal jumps in front of the vehicle). Some examples of elements that may contribute to driving behavior include acceleration constraints, deceleration constraints, speed constraints, steering constraints, suspension settings, routing preferences (e.g., scenic routes, faster routes, no highways), lighting preferences, "legal ambiguity" conduct (e.g., in a solid-green left turn situation, whether a vehicle pulls out into the intersection or waits at the intersection line), action profiles (e.g., how a vehicle turns, changes lanes, or performs a driving maneuver), and action frequency constraints (e.g., how often a vehicle changes lanes).

As will be appreciated by one skilled in the art, aspects of the present disclosure, in particular aspects of a perception system for an autonomous vehicle, described herein, may be embodied in various manners (e.g., as a method, a system, a computer program product, or a computer-readable storage medium). Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Functions described in this disclosure may be implemented as an algorithm executed by one or more hardware processing units, e.g. one or more microprocessors, of one or more computers. In various embodiments, different steps and portions of the steps of each of the methods described herein may be performed by different processing units. Furthermore, aspects of the present disclosure may take the form of a computer program product embodied in one or more computer readable medium(s), preferably non-transitory, having computer readable program code embodied, e.g., stored, thereon. In various embodiments, such a computer program may, for example, be downloaded (updated) to the existing devices and systems (e.g. to the existing perception system devices and/or their controllers, etc.) or be stored upon manufacturing of these devices and systems.

The following detailed description presents various descriptions of specific certain embodiments. However, the innovations described herein can be embodied in a multitude of different ways, for example, as defined and covered by the claims and/or select examples. In the following description, reference is made to the drawings where like reference numerals can indicate identical or functionally similar elements. It will be understood that elements illustrated in the drawings are not necessarily drawn to scale. Moreover, it will be understood that certain embodiments can include more elements than illustrated in a drawing and/or a subset of the elements illustrated in a drawing. Further, some embodiments can incorporate any suitable combination of features from two or more drawings.

The preceding disclosure describes various illustrative embodiments and examples for implementing the features and functionality of the present disclosure. While particular components, arrangements, and/or features are described below in connection with various example embodiments, these are merely examples used to simplify the present disclosure and are not intended to be limiting. It will of course be appreciated that in the development of any actual embodiment, numerous implementation-specific decisions must be made to achieve the developer's specific goals, including compliance with system, business, and/or legal constraints, which may vary from one implementation to another. Moreover, it will be appreciated that, while such a development effort might be complex and time-consuming; it would nevertheless be a routine undertaking for those of ordinary skill in the art having the benefit of this disclosure.

In the Specification, reference may be made to the spatial relationships between various components and to the spatial orientation of various aspects of components as depicted in the attached drawings. However, as will be recognized by those skilled in the art after a complete reading of the present disclosure, the devices, components, members, apparatuses, etc. described herein may be positioned in any desired orientation. Thus, the use of terms such as "above", "below", "upper", "lower", "top", "bottom", or other similar terms to describe a spatial relationship between various components or to describe the spatial orientation of aspects of such components, should be understood to describe a relative relationship between the components or a spatial orientation of aspects of such components, respectively, as the components described herein may be oriented in any desired direction. When used to describe a range of dimensions or other characteristics (e.g., time, pressure, temperature, length, width, etc.) of an element, operations, and/or conditions, the phrase "between X and Y" represents a range that includes X and Y.

Other features and advantages of the disclosure will be apparent from the description and the claims. Note that all optional features of the apparatus described above may also be implemented with respect to the method or process described herein and specifics in the examples may be used anywhere in one or more embodiments.

The 'means for' in these instances (above) can include (but is not limited to) using any suitable component discussed herein, along with any suitable software, circuitry, hub, computer code, logic, algorithms, hardware, controller, interface, link, bus, communication pathway, etc. In a second example, the system includes memory that further comprises machine-readable instructions that when executed cause the system to perform any of the activities discussed above.

What is claimed is:

1. A method for dynamically tracking cleanliness of an exterior of a vehicle, comprising:
   measuring airborne particles with an airborne particle sensor, and collecting airborne particle measurement data;
   determining total exposure of the vehicle to airborne particles based on the airborne particle measurement data over a first time window;
   determining, based in part on the total exposure, a level of cleanliness of the vehicle at the end of the first time window; and
   recording locations of airborne particle measurements.

2. The method of claim 1, further comprising updating a mapping database with airborne particle data at the recorded locations.

3. The method of claim 2, wherein the recorded locations are geographic locations.

4. The method of claim 1, further comprising determining, based on the level of cleanliness, whether to schedule a cleaning for the vehicle.

5. The method of claim 1, further comprising scheduling the cleaning for the vehicle, wherein scheduling the cleaning depends in part on expected traffic patterns.

6. The method of claim 1, further comprising scheduling the cleaning for the vehicle, wherein scheduling the cleaning depends in part on expected weather.

7. The method of claim 1, further comprising determining exposure of the vehicle to rain, and wherein determining a level of cleanliness is based in part on the exposure of the vehicle to rain.

8. The method of claim 1, wherein measuring airborne particle data comprises one of continuously measuring airborne particle data or intermittently measuring airborne particle data.

9. The method of claim 1, further comprising:
accumulating airborne particle data measurements over one or more additional time windows and adding the measurements to the total exposure to yield an updated total exposure; and
determining, based in part on the updated total exposure, the level of cleanliness of the vehicle at the end of the additional time windows.

10. The method of claim 1, further comprising cleaning the vehicle, and wherein the total exposure is reset after the cleaning.

11. A system for tracking cleanliness of an exterior of a vehicle, comprising:
a locator for determining vehicle location;
at least one sensor for measuring airborne particles;
a database for collecting airborne particle measurement data, wherein the database includes the vehicle location for each airborne particle measurement; and
a processor for determining total exposure of the vehicle to airborne particles based on the airborne particle measurement data, and determining a level of cleanliness of the vehicle.

12. The system of claim 11, wherein the database is a vehicle database, and further comprising a transmitter configured to transmit airborne particle measurement data for each location to a central mapping database.

13. The system of claim 11, wherein the processor is further configured to flag the vehicle for cleaning when the level of cleanliness exceeds a predetermined threshold.

14. The system of claim 13, further comprising a scheduler for scheduling the vehicle for cleaning when the vehicle is flagged for cleaning.

15. The system of claim 11, wherein the at least one sensor is an optical sensor including a light source and a photosensor, and wherein the photosensor has one of fixed sensitivity and adjustable sensitivity.

16. The system of claim 11, wherein the at least one sensor for measuring airborne particles is located in a sensor suite comprising multiple types of sensors.

17. The system of claim 11, wherein the at least one sensor is located at one of the front of the vehicle, the back of the vehicle, and a side of the vehicle.

18. A method for dynamically tracking cleanliness of vehicles in a fleet of vehicles, comprising:
measuring airborne particles with an airborne particle sensor and collecting airborne particle measurement data for each of the vehicles;
determining total exposure of each of the vehicles to airborne particles based on the airborne particle measurement data over a first time window;
determining for each vehicle, based in part on the total exposure, a level of cleanliness of each vehicle at the end of the first time window; and
recording location information for the collected airborne particle measurement data for each vehicle.

19. The method of claim 18, further comprising saving recorded airborne particle measurement data for each location to a central mapping database.

20. The method of claim 19, determining a route for each vehicle based in part on airborne particle measurement data in the central mapping database.

* * * * *